United States Patent
Yuan et al.

(10) Patent No.: US 6,310,212 B1
(45) Date of Patent: Oct. 30, 2001

(54) 4-SUBSTITUTED QUINOLINE DERIVATIVES

(75) Inventors: Jun Yuan, Guilford; Alan Hutchinson, Madison, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/535,825

(22) Filed: Mar. 28, 2000

(51) Int. Cl.$^7$ .................... A61K 31/55; C07D 215/16; C07D 267/02

(52) U.S. Cl. .................... 546/153; 514/218; 514/256; 514/314; 514/312; 514/313; 546/157; 546/159; 546/167; 544/333; 540/553

(58) Field of Search .................... 514/218, 256, 514/314, 312, 313; 546/153, 157, 159, 167; 544/333; 540/553

(56) References Cited

U.S. PATENT DOCUMENTS 5,792,766    8/1998   Chen et al. .

FOREIGN PATENT DOCUMENTS

| WO 95/11885 A | 5/1995 | (WO) . |
| WO 96/02509 | 2/1996 | (WO) . |

OTHER PUBLICATIONS

Yuan, CA 133:266851, 2000.*
Lakhani, CA 109:149419, 1988.*
Piero Savarino et al., "Assembled systems (X–azolopyridine)(quinoline). Bases and Salts.", Journal of Heterocyclic Chemistry, vol. 29, 1992. Pp. 185–192, XP002144891.

Giardinia et al., (1997) "Discovery of a Novel Class of Selective Non–Peptide Antagonists for the Human Neurokinin–3 Receptor. 1. Identification of the 4–Quinolincarboxamide Framework", *Journal of Medicinal Chemistry*, vol. 40. pp. 1794–1807.
Raveglia et al., (1997) "A Nobel Synthesis of 3–Halo–2–phenyquinoline–4–carboxylic Acids", *J. heterocyclic Chem.* vol. 34, pp. 557–559.

* cited by examiner

*Primary Examiner*—D. Margaret Seaman
(74) *Attorney, Agent, or Firm*—McDonnell Boehnen Hulbert & Berghoff

(57) ABSTRACT

Disclosed are compounds of the Formula I

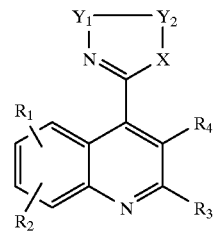

where $R_1$, $R_2$, $R_3$, $R_4$, X, $Y_1$, and $Y_2$ are defined herein. These compounds bind with high affinity to $GABA_A$ receptors. Also disclosed are pharmaceutical compositions comprising these compounds, and methods of treating patients suffering from certain central nervous system and peripheral diseases or disorders with these pharmaceutical compositions. This invention also relates to the use of such compounds in combination with one or more other CNS agents to potentiate the effects of the other CNS agents. The compounds of this invention are also useful as probes for the localization of $GABA_A$ receptors.

14 Claims, No Drawings

4-SUBSTITUTED QUINOLINE DERIVATIVES

BACKGROUND OF THE INVENTION

1. Field Of The Invention

This invention relates to quinoline derivatives, pharmaceutical compositions comprising them, and the use of such compounds in the treatment of certain central nervous system and peripheral diseases or disorders. This invention also relates to the use of such compounds in combination with one or more other CNS agents to potentiate the effects of the other CNS agents. The compounds of this invention are also useful as probes for the localization of cell surface receptors.

2. Description of the Related Art

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et. al. Neuroch. Res. 1995; 20(5):631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th}$ ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when when used in combination with $GABA_A$ selective ligands than when used alone.

SUMMARY OF THE INVENTION

Disclosed are compounds, particulary quinoline derivatives that bind to cell surface receptors. Preferred compounds of the invention bind to neurokinin and/or GABA receptors, in particular these compounds possess affinity for $GABA_A$ receptors. These compounds are therefore considered to be of use in the treatment of a broad array of diseases or disorders in patients which are characterized by modulation of $GABA_A$ receptors.

This invention provides compounds of general Formula I:

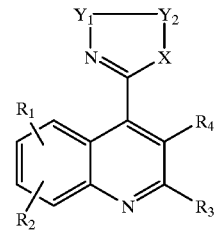

Formula I or pharmaceutically acceptable salts or pharmaceutically acceptable solvates thereof, wherein in $R_1$, $R_2$, $R_3$, $R_4$, X, $Y_1$ and $Y_2$ are hereinafter defined.

Preferred compounds of this invention are ligands for GABA receptors, $GABA_A$ receptors, and are useful in the treatment of a wide range of diseases or disorders including, but not limited to depression, anxiety, sleep disorders, cognitive disorders, low alertness, psychosis, obesity, pain, Parkinson's disease, Alzheimer's disease, neurodegenerative diseases, movement disorders, Down's syndrome, and benzodiazepine overdoses.

The invention also provides pharmaceutical compositions comprising compounds of Formula I. The invention further comprises a method of treating a patient suffering from certain central nervous system and peripheral diseases or disorders with effective concentration of a compound of the invention. Treatment of humans, domesticated companion animals (pets) or livestock animals suffering such conditions with an effective amount of a compound of the invention is contemplated by the invention.

Packaged pharmaceutical compositions including instructions for use of the composition are also included.

In a separate aspect, the invention provides a method of potentiating the actions of other CNS active compounds. This method comprises administering an effective amount of a compound of the invention with another CNS active compound.

The invention furthermore provides methods of using compounds of this invention as positive controls in assays for receptor activity and using appropriately labeled compounds of the invention as probes for the localization of receptors, particularly $GABA_A$ receptors, in tissue sections.

DETAILED DESCRIPTION OF THE INVENTION

This invention relates to quinoline derivatives, pharmaceutical compositions comprising them, and the use of such compounds in the treatment of central nervous system and peripheral diseases or disorders.

Accordingly, a broad embodiment of the invention is directed to compounds of Formula I:

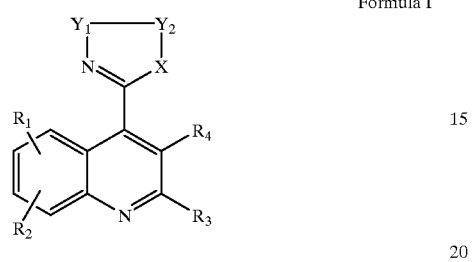

Formula I and the pharmaceutically acceptable salts and pharmaceutically acceptable solvates thereof, wherein:

$R_1$ is selected from:
hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl),
wherein said $C_{1-6}$ alkyl is straight, branched or cyclic, may contain one or two double or triple bonds, and is unsubstituted or substituted with one or more substituents selected from: hydroxy, oxo, fluoro, amino, $C_{1-3}$ alkoxy;

$R_2$ and $R_3$ are independently selected from the groups consisting of:
(1) $C_{1-8}$ alkyl, wherein said $C_{1-8}$ alkyl is straight, branched or cyclic, may contain one or two double or triple bonds, and is unsubstituted or substituted with one or more of the substituents selected from:
 (i) hydroxy,
 (ii) oxo,
 (iii) fluoro,
 (iv) amino,
 (v) $Ar_1$, wherein $Ar_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from:
  hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl),
  wherein $C_{1-6}$ alkyl, is defined as above,
 (vi) —NR$_5$R$_6$, wherein $R_5$ and $R_6$ are independently selected at each occurrence from:
  (a) hydrogen,
  (b) $C_{1-6}$ alkyl, wherein $C_{1-6}$ alkyl is as defined above,
  (c) —(CH$_2$)n-Ar$_1$, wherein n is independently selected at each occurrence from 0, 1 or 2,
  or the groups $R_5$ and $R_6$ are joined together to form a 4- to 8-membered ring may contain one or two double bonds, or one or two oxo, or one or two O, S or N—$R_7$ wherein $R_7$ is independently selected at each occurrence from hydrogen, $C_{1-6}$ alkyl, —(CH$_2$)n-Ar$_1$,
 (vii) —OR$_5$, wherein $R_5$ is as defined above,
 (viii) —CONR$_5$R$_6$ wherein $R_5$ and $R_6$ are as defined above,
 (ix) —CO$_2$ R$_5$, wherein said $R_5$ is as defined above;
(2) $Ar_2$, wherein $Ar_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:
 hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl),
 wherein said $C_{1-8}$ alkyl is as defined above;
(3) —NR$_8$R$_9$, wherein $R_8$ and $R_9$ are independently selected at each occurrence from:
 (a) hydrogen,
 (b) $Ar_2$,
 (c) $C_{1-8}$ alkyl, wherein said $C_{1-8}$ alkyl is as defined above; or the groups $R_8$ and $R_9$ are joined together to form a 4- to 8-membered ring which ring of which the 4- to 8-membered ring may contain one or more double bonds, one or more oxo, one or more O, S(O)n, N—$R_7$ wherein n and $R_7$ are as defined above; or one or more groups selected from the group consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO ($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$ ($C_{1-8}$ alkyl), —CON ($C_{1-8}$ alkyl)($C_{1-8}$ alkyl), —CO$_2$($C_{1-8}$ alkyl), —S($C_{1-8}$ alkyl), —SO($C_{1-8}$ alkyl), and —SO$_2$($C_{1-8}$ alkyl),
(4) —OR$_8$;

$R_4$ is selected from:
hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$ ($C_{1-8}$ alkyl), —NHSO$_2$($C_{1-8}$ alkyl), —N($C_{1-6}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), —SO$_2$($C_{1-8}$ alkyl), and Ar$_2$;

X is N—R$_1$, wherein R$_{10}$ is $C_{1-8}$ alkyl;

Y$_1$ is —CR$_{11}$R$_{12}$—, —CR$_{11}$R$_{12}$(CH$_2$)$_p$—, or (CH$_2$)$_p$CR$_{11}$R$_{12}$—; where p is 0, 1, or 2;

Y$_2$ is —CR$_{11}$R$_{12}$—;

R$_{11}$ and R$_{12}$ are independently selected at each occurrence from:
(1) hydrogen, and
(2) $C_{1-8}$ alkyl; or R$_{10}$ and R$_{11}$ are joined to form a 5- to 8-membered ring which may contain one or more double bonds; one O, S(O)n, or N—R$_7$ wherein n and R$_7$ are as defined above; and which may be substituted with one or more of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), or —SO($C_{1-8}$ alkyl).

Preferred compounds of the invention include compounds of Formula IA

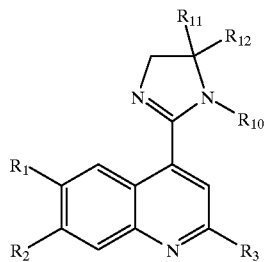

Formula IA and the pharmaceutically acceptable salts and solvates thereof, wherein: R$_1$, R$_2$, R$_3$, R$_{10}$, R$_{11}$ and R$_{12}$ are as defined for Formula I.

More preferred compounds of the invention include compounds of Formula IB

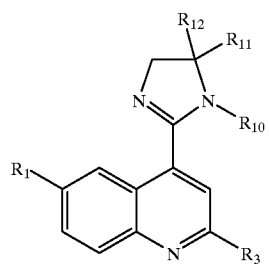

Formula IB and the pharmaceutically acceptable salts and solvates thereof, wherein:

R$_1$ is hydrogen or fluorine; and

R$_3$, R$_{10}$, R$_{11}$ and R$_{12}$ are as defined for Formula I.

Particularly preferred compounds of Formula IB are those compounds wherein:

R$_{10}$ is $C_{1-8}$alkyl; and

R$_{11}$ is hydrogen or $C_{1-8}$ alkyl.

Other preferred compounds of Formula IB are those compounds wherein:

R$_{10}$ and R$_{11}$ are joined to form a 5- to 8-membered ring which may contain one or more double bonds; one O, S(O)n, or N—R$_7$ wherein n and R$_7$ are as defined above with regard to Formula I in claim 1; and which may be substituted with one or more of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO ($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), and —SO($C_{1-8}$ alkyl).

Yet other preferred compounds of the invention are compounds of Formula IC,

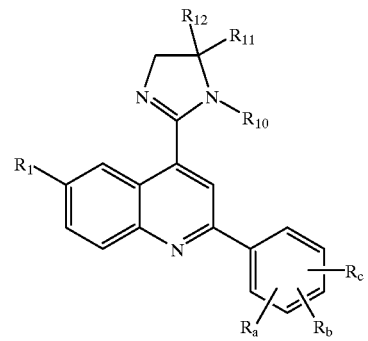

Formula IC and the pharmaceutically acceptable salts and solvates thereof, wherein R$_a$, R$_b$, and R$_c$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —CON($C_{1-6}$ alkyl)($C_{1-6}$ alkyl), —CO$_2$($C_{1-6}$ alkyl), wherein $C_{1-6}$alkyl is as defined above;

R$_1$ is hydrogen or fluorine;

R$_{10}$ is $C_{1-8}$ alkyl; and

R$_{11}$ and R$_{12}$ are independently hydrogen or $C_{1-8}$ alkyl.

Still other preferred compounds of the invention are compounds of Formula ID

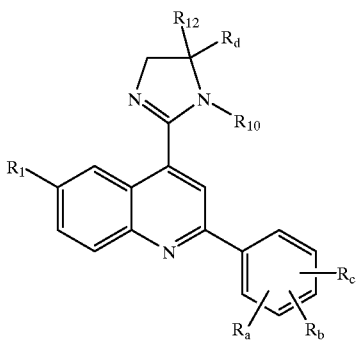

Formula ID and the pharmaceutically acceptable salts and solvates thereof,
wherein:

$R_a$, $R_b$, and $R_c$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —CON($C_{1-6}$ alkyl)($C_{1-6}$ alkyl), —CO$_2$($C_{1-6}$ alkyl), wherein $C_{1-6}$alkyl is as defined above;

$R_1$ is hydrogen or fluorine;

$R_{12}$ is hydrogen or $C_{1-8}$ alkyl; and $R_d$ and $R_{10}$ together form an alkylene group of from 3–5 carbon atoms each of which is optionally substituted with methyl or ethyl.

In certain situations, the compounds of the present invention have asymmetric centers and this invention includes all of the optical isomers and mixtures thereof.

In addition, compounds with carbon-carbon double bonds may occur in Z- and E-forms with all isomeric forms of the compounds being included in the present invention.

When any variable (e.g. alkyl, Ar$_1$, Ar$_2$, R$_5$, R$_6$, R$_8$, R$_9$, R$_{11}$, R$_{12}$, etc.) occurs more than one time in Formula I, its definition on each occurrence is independent of its definition at every other occurrence.

As used herein, the term "alkyl" includes straight or branched chain alkyl groups and cycloalkyl groups that also may contain double or triple bonds. Examples of "alkyl" include methyl, ethyl, propyl, isopropyl, butyl, iso-, sec- and tert-butyl, pentyl, hexyl, heptyl, 3-ethylbutyl, cyclopropyl, cyclobutyl, cyclopentyl, cyclohexyl, cycloheptyl, norbornyl, and the like. Where the number of carbon atoms is designed the alkyl group includes that number of carbon atoms. When reference is made herein to $C_{1-6}$ alkyl which it may contain one or two double or triple bond it is understood that at least two carbons are present in the alkyl for one double or triple bond, and at least four carbons for two double or triple bonds.

The term "alkoxy" represents an alkyl group of indicated number of carbon atoms attached through an oxygen bridge, such as methoxy, ethoxy, propoxy and isopropoxy.

By the term "halogen" is meant fluorine, chlorine, bromine, and iodine.

The term "monocyclic" includes, but is not limited to cyclopentyl, cyclohexyl or cycloheptyl; "bicyclic" includes, but is not limited to indanyl, tetrahydronaphthyl, chromanyl benzo[a][7]annulenyl, bicyclo[4.4.0]decanyl, bicyclo[4,3.0] nonanyl, bicyclo[3.3.0] octanyl; "tricyclic" includes, but is not limited to dibenzoannulenyl, dibenzoxepanyl, dibezothiepanyl.

As used herein, the terms "patients" refers to humans as well as other mammals including pets such as dogs and cats and livestock such as cattle and sheep.

This invention also includes methods for using compounds of Formula I to treat diseases or disorders in patients in which mediation by GABA$_A$ receptors is of importance.

Preferred compounds of this invention are ligands for GABA receptors, in particular the benzodiazepine site of GABA$_A$ receptors, and are useful in the treatment of a wide range of diseases or disorders of the central nervous system (CNS) and periphery in mammals in which modulation of GABA$_A$ receptors is of importance. These include depression, anxiety, panic disorder, obsessive compulsive disorder, sleep disorders, cognitive disorders, low alertness, neurodegenerative disorders such as dementia, Alzheimer's diseases, Parkinson's disease, Huntington's disease, Down's syndrome, benzodiazepine overdoses, stress related somatic disorders. Compounds contained in the invention are also useful for the diagnosis of disorders involving mediation by GABA$_A$ receptors in patients.

Non-toxic pharmaceutical salts include salts, include, but not limited to salts with inorganic acids such as hydrochloride, sulfate, phosphate, diphosphate, hydrobromide, and nitrite or salts with an organic acid such as malate, maleate, fumarate, tartrate, succinate, citrate, acetate, lactate, methanesulfonate, p-toluenesulfonate, 2-hydroxyethylsulfonate, pamoate, salicylate and stearate. Similarly, pahrmaceutically acceptable cations include, but are not limited to sodium, potassium, calcium, aluminum, lithium and ammonium.

The present invention also encompasses the prodrugs of the compounds of Formula I. Those skilled in the art will recognize various synthetic methodologies (references by N. Bodor, Drugs of the Future, 1981, 6, 165–182, or H. Bundgaard, Advanced Drug Delivery Reviews, 1989, 3, 39–65) which may be employed to prepare non-toxic pharmaceutically acceptable prodrugs of the compounds encompassed by Formula I.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety or depression a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to $GABA_A$ receptor modulation, e.g., treatment of cognitive deficits, anxiety or depression by $GABA_A$ receptor modulation. The packaged pharmaceutical compositions include a container holding a therapeutically effective amount of at least one $GABA_A$ receptor modulator as described supra and instructions (e.g., labeling) indicating the the contained $GABA_A$ receptor ligand is to be used for treating a disorder responsive to $GABA_A$ receptor modulation in the patient.

The present invention also pertains to methods for altering the signal-tranducing activity of $GABA_A$ receptors, said method comprising exposing cells expressing such receptor to an effective amount of a compound of the invention. A method of inhibiting the binding of a benzodiazepine compound to the benzodiazepine site of the $GABA_A$ receptor, comprising contacting a compound of Formula I with cells expressing such a receptor in the presence of a the benzodiazepine compound, wherein the compound is present at a concentration sufficient to inhibit benzodiazepine compound binding to cells expressing a cloned human $GABA_A$ receptor.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5-HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in an analogous fashion to that disclosed in Da-Rocha, et al., *J. Psychopharmacology* (1997) 11(3) 211–218; Smith, et al., *Am. J. Psychiatry* (1998) 155(10) 1339–45; and Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl)methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

Preferred compounds of the invention show selectivity for the $GABA_A$ receptor as compared to the NK-3 receptor as measured by standard assays for NK-3 and $GABA_A$ Receptor binding (See example 13 for a standard assay of NK-3 receptor binding and example 14 for a standard assay of $GABA_A$ receptor binding).

Preferred compounds exhibit a 10-fold greater affinity for the $GABA_A$ receptor, more preferred compounds exhibit a 100-fold greater affinity for the $GABA_A$ receptor, and most preferred compounds exhibit a 1000-fold greater affinity for the $GABA_A$ receptor in a standard assay of GABAA receptor binding than for the NK-3 receptor in a standard assay of Nk-3 receptor binding.

COMPOUND PREPARATION

Several methods for preparing the compounds of this invention are illustrated in the following Scheme I, II and III. The synthesis of compounds of Formula II is described in detail in the several publications including Giardina et. al. J. Med. Chem. 1997, 40, 1794–1807 and Giardina et. al. J. Heterocyclic Chem., 1997, 34, 557–559 and references cited therein. It will be recognized by those skilled in the art that the structures of Formula III, IV, and V can be readily synthesized from various readily available amino acids. Alternatively, various readily available ketones and aldeydes can be converted to the corresponding aminocyanides and cyanohydrins and subsequently reduced to the desired diamines and aminoalcohols. Those skilled in the art will recognize that in certain instances it will be necessary to utilize compounds of Formula II and Formula III bearing protecting groups and that these groups can be removed in a subsequent reaction to yield compounds of Formula I as described in "Protective Groups in Organic Synthesis", 2nd Ed., Greene, T. W. and related publications.

Scheme I

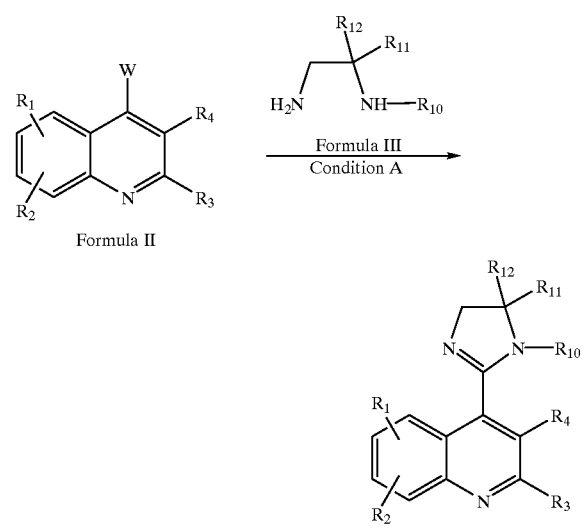

wherein $R_1$, $R_2$, $R_3$, $R_4$, $R_{10}$, $R_{11}$, and $R_{12}$ are as defined above, W is —$CO_2H$, —$CO_2Me$, —$CO_2Et$, —$C(OEt)_3$, —C=NHOMe, —C=NHOEt, —$CSNH_2$, —C=$NHNH_2$, or —CN.

Condition A includes, but is not limited to, heating with or without a solvent such as toluene, ethanol, or xylene at 40–250° C.; heating with AlMe₃ in a solvent such as toluene at 80–120° C. and, occasionally, continued heating in the presence of Lawesson's reagent; or stirring at room temperature in presence of triphenylphosphine, CCl₄ and a base such as triethylamine or diisoprpylethylamine in a solvent such as acetonitrile or a mixture of solvents such as acetonitrile-pyridine.

Scheme II

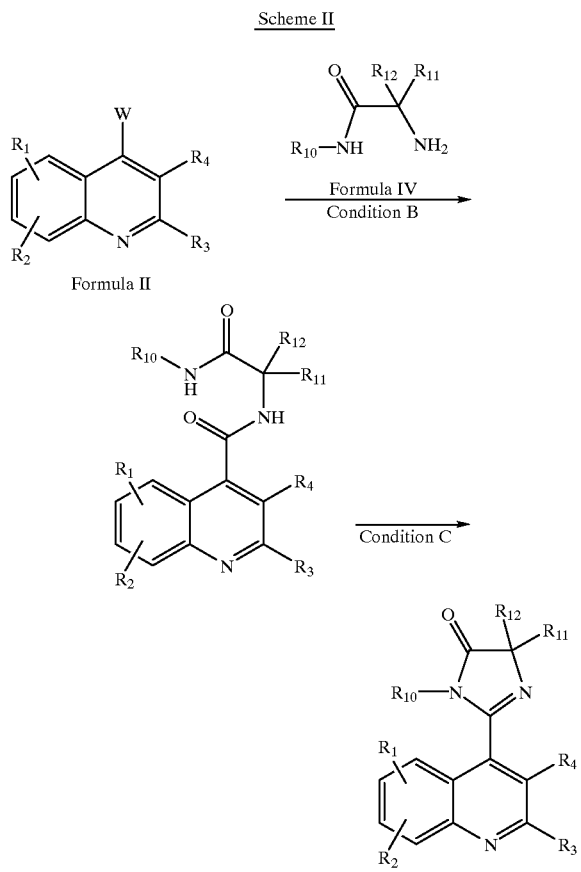

wherein $R_1$, $R_2$, $R_3$, $R_4$, $R_{10}$, $R_{11}$, and $R_{12}$ are as defined above, W is —COCl or —CO₂H.

Condition B includes, but is not limited to, reaction of the amine with acid chloride (W=COCl) in the presence of base as well as amide bond forming conditions such as those employing the BOP reagent in the presence of base.

Condition C includes, but is not limited to, treatment with sodium methoxide in the presence of methanol as solvent.

Scheme III wherein $R_1$, $R_2$, $R_3$, $R_4$, $R_{11}$, $R_{12}$ are as defined above, W is —CO₂H, —CO₂Me, —CO₂Et, —C(OEt)₃, —C=NHOMe, —C=NHOEt, —CSNH₂, or —C=NHNH₂.

Condition A includes, but is not limited to, heating with or without a solvent such as toluene, ethanol, or xylene at 40–250° C.; heating with AlMe₃ in a solvent such as toluene at 80–120° C. and, ocassionally, continued heating in the presence of Lawesson's reagent; or stirring at room temperature in presence of triphenylphosphine, CCl₄ and a base such as triethylamine or diisoprpylethylamine in a solvent such as acetonitrile or a mixture of solvents such as acetonitrilepyridine.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be obvious to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

S-3-(2-phenylquinolin-4-yl)-5,6,7,7a-tetrahydro-1H-pyrrolo[1,2-c]imidazole

A solution of trimethylaluminum in toluene (2.0 M, 1 mL) is added dropwise to a stirred solution of (S)-2-(aminomethyl)pyrrolidine (200 mg, 2 mmol) in 5 mL of toluene at below 10° C. under nitrogen. The resulting solution is heated at 60° C. for one hour and cooled to room temperature. 2-Phenyl-4-quinolinecarboxylate (263 mg, 1 mmol) is added to the solutuion once. The reaction mixture is refluxed for 16 hours under nitrogen. After cooling, the solution is treated with 1 mL of water, diluted with lmL of methanol and 1 mL of methylene chloride, and refluxed for 15 minutes. After separation of organic solvent and solvent evaporation, the residue is purified over silica gel chromatography eluting with 5–10% MeOH/$CH_2Cl_2$ to give 76 mg of the titled compound. $^1$H NMR ($CDCl_3$) δ 1.5–2.1 (m,3 H), 2.95–3.20 (m, 2 H), 3.98–4.30 (m, 3 H), 2.13 (m, 2 H), 7.40–7.60 (m, 4 H), 7.75 (t, 1 H), 8.15 (s, 1 H), 8.22 (m, 3 H), 8.53 (d, 1 H). MS ($ES^+$): 314 $[MH]^+$.

Examples 2–12

Accordingly, the following compounds are prepared by analogous procedure described for example 1.

EXAMPLE 2

S-3-[2-(6-Fluorophenyl)quinolin-4-yl]-5,6,7,7a-tetrahydro-1H-pyrrolo[1,2-c]imidazole.

EXAMPLE 3

S-3-[2-(2-Fluorophenyl)quinolin-4-y]-5,6,7,7a-tetrahydro-1H-pyrrolo[1,2-c]imidazole.

EXAMPLE 4

S-3-[2-(4-Fluorophenyl)quinolin-4-y])-5,6,7,7a-tetrahydro-1H-pyrrolo[1,2-c]imidazole.

EXAMPLE 5

S-3-[2-(2,3-Difluorophenyl)quinolin-4-yl]-5,6,7,7a-tetrahydro-1H-pyrrolo[1,2-c]imidazole

EXAMPLE 6

S-3-[2-(2,4-Difluorophenyl)quinolin-4-yl]-5,6,7,7a-tetrahydro-1H-pyrrolo[1,2-c]imidazole

EXAMPLE 7

S-3-[2-(3-thienyl)quinolin-4-yl)-5,6,7,7a-tetrahydro-1H-pyrrolo[1,2-c]imidazole

EXAMPLE 8

1-Methyl-2-(2-phenylquinolin-4-yl)-4,5-dihydro-1H-Imidazole.

EXAMPLE 9

1-Ethyl-2-(2-phenylquinolin-4-yl)-4,5-dihydro-1H-Imidazole.

EXAMPLE 10

1,5-Dimethyl-2-(2-phenylquinolin-4-yl)-4,5-dihydro-1H-Imidazole.

EXAMPLE 11

1-Methyl-2-(2-phenylquinolin-4-yl)-1,4,5,6-tetrahydro-Pyrimidine

EXAMPLE 12

1-Ethyl-2-(2-phenylquinolin-4-yl)-1,4,5,6-tetrahydro-Pyrimidine.

EXAMPLE 13

Assay For NK-3 Recptor Binding Activity

The following assay is a standard assay for NK-3 receptor binding activity. Assays are performed as described in Krause et al (Proc. Natl. Acad. Sci. USA 94: 310–315, 1997). The NK-3 receptor complementary DNA was cloned from human hypothalamic RNA using standard procedures. The receptor cDNA was inserted into the expression vector $pM^2$ to transfect the mammalian Chinese hamster ovary cell line, and a stably expressing clonal cell line was isolated, characterized and used for the current experiments. Cells are grown in minimal essential medium alpha containing 10% fetal bovine serum and 250 μg/ml G418. Cells were liberated from cell culture plates with No-zyme (PBS base, JRH Biosciences), and harvested by low speed centrifugation. The cell pellet was homogenized in TBS (0.05 m TrisHCl, 120 mM NaCl, pH 7.4) with a Polytron homogenizer at setting 5 for 20 seconds, and total cellular membranes were isolated by centrifugation at 47,500×g for 10 minutes. The membrane pellet was resuspended by homogenization with the Polytron as above, and the membranes were isolated by centrifugation at 47,500×g for 10 minutes. This final membrane pellet was resuspended in TBS at a protein concentration of 350 μg/ml.

Receptor binding assays contain a total volume of 200 μl containing 50 μg membrane protein, 0.05–0.15 nM 125I-methylPhe7-neurokinin B, drug or blocker in TBS containing 1.0 mg/ml bovine serum albumen, 0.2 mg/ml bacitracin, 20 μg/ml leupeptin and 20 μg/ml chymostatin. Incubations are carried out for 2 hours at 4° C., and the membrane proteins are harvested by passing the incubation mixture by rapid filtration over presoaked GF/B filters to separate bound from free ligand. The filters are presoaked in TBS containing 2% BSA and 0.1% Tween 20. After filtration of the incubation mixture, filters are rinsed 4 times with ice-cold TBS containing 0.01% sodium dodecyl sulfate and radioactivity is quantitated in a β-plate scintillation counter. One μM methylPhe7-neurokinin B is added to some tubes to determine nonspecific binding. Data are collected in duplicate determinations, averaged, and the percent inhibition of total specific binding is calculated. The total specific binding is the total binding minus the nonspecific binding. In many cases, the concentration of unlabeled drug is varied and total displacement curves of binding is carried out. Data are converted to a form for the calculation of $IC_{50}$ and Hill coefficient (nH).

EXAMPLE 14

Assay for $GABA_A$ Receptor Binding

The following assay is a standard assay for $GABA_A$ receptor binding.

The high affinity and high selectivity of compounds of this invention for the benzodiazepine site of the $GABA_A$ receptor is confirmed using the binding assay described in Thomas and Tallman (*J. Bio. Chem.* 1981; 156:9838–9842, and *J. Neurosci.* 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containing 100 μl of tissue homogenate, 100 μl of radioligand, (0.5 nM $^3$H-Ro15-1788 [$^3$H-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 with 10 μM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}$M to $10^{-5}$M obtained per curve by the method described above for determining percent inhibition. $K_i$ values are calculated according the Cheng-Prussof equation. When tested in this assay compounds of the invention exihibit $K_i$ values of less than 1 μM, preferred compounds of the invention have $K_i$ values of less than 500 nM and more compounds of the invention have $K_i$ values of less than 100 nM.

EXAMPLE 15

Assay for GABA$_A$ Receptor Functional Activity Electrophysiology

The following assay is used to determine if a compound of the invention act as an agonist, an antagonist, or an inverse agonist at the benzodiazepine site of the GABA$_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\beta_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

EXAMPLE 16

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 17

Use of Compounds of the Invention as Probes for GABA$_A$ Receptors in Cultured Cells and Tissue Samples Receptor autoradiography (receptor mapping) of GABA$_A$ receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made

What is claimed is:
1. A compound of the formula:

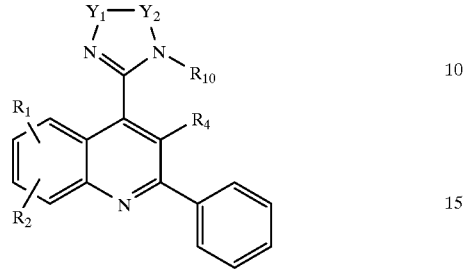

or a pharmaceutically acceptable salt or pharmaceutically acceptable solvate thereof, wherein:

$R_1$ is selected from
hydrogen, halogen, hydroxy, $C_{1-6}$ alkyl, —O($C_{1-6}$ alkyl), —$NO_2$, —CN, —$SO_2NH_2$, —$SO_2NH(C_{1-6}$ alkyl), —$SO_2N(C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$ ($C_{1-6}$ alkyl), —$NHSO_2(C_{1-6}$ alkyl), —N($C_{1-6}$ alkyl)$SO_2(C_{1-6}$ alkyl), —$SO_2NHCO(C_{1-6}$ alkyl), —$CONHSO_2(C_{1-6}$ alkyl), —CON($C_{1-6}$ alkyl)($C_{1-6}$ alkyl), —$CO_2(C_{1-6}$ alkyl), —S($C_{1-6}$ alkyl), —SO($C_{1-6}$ alkyl), or —$SO_2(C_{1-6}$ alkyl),
wherein said $C_{1-6}$ alkyl is straight, branched or cyclic, may contain one or two double or triple bonds, and is unsubstituted or substituted with one or more substituents selected from hydroxy, oxo, fluoro, amino, $C_{1-3}$ alkoxy;

$R_2$ is
(1) $C_{1-8}$ alkyl, wherein said $C_{1-8}$ alkyl is straight, branched or cyclic, may contain one or two double or triple bonds, and is unsubstituted or substituted with one or more of the substituents selected from:
  (i) hydroxy,
  (ii) oxo,
  (iii) fluoro,
  (iv) amino,
  (v) $Ar_1$, wherein $Ar_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from:
    hydrogen, halogen, hydroxy, $C_{1-6}$ alkyl, —O($C_{1-6}$ alkyl), —$NO_2$, —CN, —$SO_2NH_2$, —$SO_2NH(C_{1-6}$ alkyl), —$SO_2N(C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2(C_{1-6}$ alkyl), —$NHSO_2(C_{1-6}$ alkyl), —N($C_{1-6}$ alkyl)$SO_2(C_{1-6}$ alkyl), —$SO_2NHCO(C_{1-6}$ alkyl), —$CONHSO_2(C_{1-6}$ alkyl), —CON($C_{1-6}$ alkyl)($C_{1-6}$ alkyl), —$CO_2(C_{1-6}$ alkyl), —S($C_{1-6}$ alkyl), —SO($C_{1-6}$ alkyl), or —$SO_2(C_{1-6}$ alkyl), wherein $C_{1-6}$ alkyl, is defined as above,
  (vi) —$NR_5R_6$, wherein $R_5$ and $R_6$ are independently selected at each occurrence from:
    (a) hydrogen,
    (b) $C_{1-6}$ alkyl, wherein $C_{1-6}$ alkyl is as defined above,
    (c) —$(CH_2)n$-$Ar_1$, wherein n is independently selected at each occurrence from 0, 1 or 2,
    (d) or the groups $R_5$ and $R_6$ are joined together to form a 4- to 8-membered ring which may contain one or two double bonds, or one or two oxo, or one or two O, S or N—$R_7$ wherein $R_7$ is independently selected at each occurrence from hydrogen, $C_{1-6}$ alkyl, —$(CH_2)n$-$Ar_1$,
  (vii) —$OR_5$, wherein $R_5$ is as defined above,
  (viii) —$CONR_5R_6$ wherein $R_5$ and $R_6$ are as defined above,
  (ix) —$CO_2 R_5$, wherein said $R_5$ is as defined above;
(2) $Ar_2$, wherein $Ar_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and is unsubstituted and substituted with one or more substituents selected from:
  hydrogen, halogen, hydroxy, $C_{1-8}$ alkyl, —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2(C_{1-8}$ alkyl), —$NHSO_2(C_{1-8}$ alkyl), —N($C_{1-8}$ alkyl)$SO_2(C_{1-8}$ alkyl), —$SO_2NHCO (C_{1-8}$ alkyl), —$CONHSO_2(C_{1-8}$ alkyl), —CON($C_{1-8}$ alkyl)($C_{1-8}$ alkyl), —$CO_2(C_{1-8}$ alkyl), —S($C_{1-8}$ alkyl), —SO($C_{1-8}$ alkyl), or —$SO_2(C_{1-8}$ alkyl), wherein said $C_{1-8}$ alkyl is as defined above;
(3) —$NR_8R_9$, wherein $R_8$ and $R_9$ are independently selected at each occurrence from:
  (a) hydrogen,
  (b) $Ar_2$,
  (c) $C_{1-8}$ alkyl, wherein said $C_{1-8}$ alkyl is as defined above;
  or the groups $R_8$ and $R_9$ are joined together to form a which ring may contain one or more double bonds; one or more oxo; one or more O, S(O)n, N—$R_7$ wherein n and $R_7$ are as defined above; or one or more of hydroxy, halogen, amino, $C_{1-8}$ alkyl, —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO ($C_{1-8}$ alkyl), —N($C_{1-8}$ alkyl)$CO_2(C_{1-8}$ alkyl), —$NHSO_2(C_{1-8}$ alkyl), —N($C_{1-8}$ alkyl)$SO_2(C_{1-8}$ alkyl), —$SO_2NHCO(C_{1-8}$ alkyl), —$CONHSO_2$ ($C_{1-8}$ alkyl), —CON($C_{1-8}$ alkyl)($C_{1-8}$ alkyl), —$CO_2(C_{1-8}$ alkyl), —S($C_{1-8}$ alkyl), —SO($C_{1-8}$ alkyl) or —$SO_2(C_{1-8}$ alkyl); or
(4) —$OR_8$;

$R_4$ is selected from
hydrogen, halogen, hydroxy, $C_{1-8}$ alkyl, —O($C_{1-8}$ alkyl), —$NO_2$, —CN, —$SO_2NH_2$, —$SO_2NH(C_{1-8}$ alkyl), —$SO_2N(_{1-8}$ alkyl)($C_{1-8}$ alkyl), amino, —NH ($_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2(C_{1-8}$ alkyl), —$NHSO_2(C_{1-8}$ alkyl), —N($C_{1-6}$ alkyl)$SO_2$ ($C_{1-8}$ alkyl), —$SO_2NHCO(C_{1-8}$ alkyl), —$CONHSO_2(C_{1-8}$ alkyl), —CON($C_{1-8}$ alkyl)($C_{1-8}$ alkyl), —CO$_2$(C$_{1-8}$ alkyl), —S(C$_{1-8}$ alkyl), —SO(C$_{1-8}$ alkyl), —SO$_2$(C$_{1-8}$ alkyl), and Ar$_2$;

X is N—R$_{10}$, wherein R$_{10}$ is C$_{1-8}$ alkyl or an electron pair;

Y$_1$ is —CR$_{11}$R$_{12}$—, —CR$_{11}$R$_{12}$(CH$_2$)$_p$—, or (CH$_2$)$_p$CR$_{11}$R$_{12}$—; where p is 0, 1, or 2;

Y$_2$ is —CR$_{11}$R$_{12}$—;

R$_{11}$ and R$_{12}$ are independently selected at each occurrence from:
(1) hydrogen, and
(2) C$_{1-8}$ alkyl; or R$_{10}$ and R$_{11}$ may be joined to form a 5- to 8-membered ring which may contain one or more double bonds; one O, S(O)n, or N—R$_7$ wherein n and R$_7$ are as defined above; and which may be substituted with one or more of hydroxy, halogen, amino, C$_{1-8}$ alkyl, —O(C$_{1-8}$ alkyl), —NO$_2$, —CN, —SO$_2$NH$_2$, —SO$_2$NH(C$_{1-8}$ alkyl), —SO$_2$N(C$_{1-8}$ alkyl)(C$_{1-8}$ alkyl), amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —N(C$_{1-8}$ alkyl)CO$_2$(C$_{1-8}$ alkyl), —NHSO$_2$(C$_{1-8}$ alkyl), —N(C$_{1-8}$ alkyl)SO$_2$(C$_{1-8}$ alkyl), —SO$_2$NHCO(C$_{1-8}$ alkyl), —CONHSO$_2$(C$_{1-8}$ alkyl), —CON(C$_{1-8}$ alkyl)(C$_{1-8}$ alkyl), —CO$_2$(C$_{1-8}$ alkyl), —S(C$_{1-8}$ alkyl), and —SO(C$_{1-8}$ alkyl).

2. A compound according to claim 1, where —Y$_1$—Y$_2$— represents —CR$_{11}$R$_{12}$—, R$_4$ is hydrogen, R$_1$ is at the 6-position of the quinoline ring and R$_2$ is at the 7 position of the quinoline ring.

3. A compound according to claim 1, wherein R$_2$ is hydrogen.

4. A compound according to claim 3, wherein
R$_1$ is hydrogen or fluorine;
R$_{10}$ is C$_{1-8}$ alkyl; and
R$_{11}$ is hydrogen or C$_{1-8}$ alkyl.

5. A compound according to claim 4, wherein
R$_{10}$ and R$_{11}$ together with the carbon atom to which they are attached form a 5- to 8-membered ring which may contain one or more double bonds; and which may be substituted with one or more of hydroxy, halogen, amino, C$_{1-8}$ alkyl, —O(C$_{1-8}$ alkyl), —NO$_2$, —CN, —NH(C$_{-8}$ alkyl), and —N(C$_{1-8}$ alkyl)(C$_{1-8}$ alkyl).

6. A compound according to claim 1, wherein
R$_{10}$ is C$_1$–C$_8$ alkyl; and
R$_{11}$ and R$_{12}$ are independently hydrogen or C$_{1-8}$ alkyl.

7. A compound according to claim 1, which is: S-3-(2-phenylquinolin-4-yl)-5,6,7,7a-tetrahydro-1H-pyrrolo[1,2-c]imidazole.

8. A compound according to claim 1, which is selected from:
S-3-[2-(6-Fluorophenyl)quinolin-4-yl]-5,6,7,7a-tetrahydro-1H-pyrrolo[1,2-c]imidazole;
S-3-[2-(2-Fluorophenyl)quinolin-4-y]-5,6,7,7a-tetrahydro-1H-pyrrolo[1,2-c]imidazole;
S-3-[2-(4-Fluorophenyl)quinolin-4-y])-5,6,7,7a-tetrahydro-1H-pyrrolo[1,2-c]imidazole;
S-3-[2-(2,3-Difluorophenyl)quinolin-4-yl]-5,6,7,7a-tetrahydro-1H-pyrrolo[1,2-c]imidazole;
S-3-[2-(2,4-Difluorophenyl)quinolin-4-yl]-5,6,7,7a-tetrahydro-1H-pyrrolo[1,2-c]imidazole;
S-3-[2-(3-thienyl)quinolin-4-yl)-5,6,7,7a-tetrahydro-1H-pyrrolo[1,2-c]imidazole;
1-Methyl-2-(2-phenylquinolin-4-yl)-4,5-dihydro-1H-Imidazole;
1-Ethyl-2-(2-phenylquinolin-4-yl)-4,5-dihydro-1H-Imidazole;
1,5-Dimethyl-2-(2-phenylquinolin-4-yl)-4,5-dihydro-1H-Imidazole;
1-Methyl-2-(2-phenylquinolin-4-yl)-1,4,5,6-tetrahydro-Pyrimidine; and
1-Ethyl-2-(2-phenylquinolin-4-yl)-1,4,5,6-tetrahydro-Pyrimidine.

9. A pharmaceutical composition comprising a compound according to claim 1 combined with at least one pharmaceutically acceptable carrier or excipient.

10. A compound of the formula:

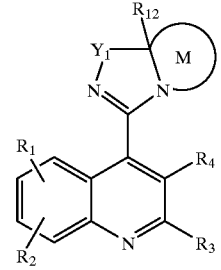

or a pharmaceutically acceptable salt or solvate thereof wherein:

R$_1$ is selected from hydrogen, halogen, hydroxy, C$_{1-6}$ alkyl, —O(C$_{1-6}$ alkyl), —NO$_2$, —CN, —SO$_2$NH$_2$, —SO$_2$NH(C$_{1-6}$ alkyl), —SO$_2$N(C$_{1-6}$ alkyl)(C$_{1-6}$ alkyl), amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —NHSO$_2$(C$_{1-6}$ alkyl), —N(C$_{1-6}$ alkyl)SO$_2$(C$_{1-6}$ alkyl), —SO$_2$NHCO(C$_{1-6}$ alkyl), —CONHSO$_2$(C$_{1-6}$ alkyl), —CON(C$_{1-6}$ alkyl)(C$_{1-6}$ alkyl), —CO$_2$(C$_{1-6}$ alkyl), —S(C$_{1-6}$ alkyl), —SO(C$_{1-6}$ alkyl), or —SO$_2$(C$_{1-6}$ alkyl),
wherein said C$_{1-6}$ alkyl is straight, branched or cyclic, may contain one or two double or triple bonds, and is unsubstituted or substituted with one or more substituents selected from hydroxy, oxo, fluoro, amino, C$_{1-3}$ alkoxy;

R$_2$ and R$_3$ are independently selected from
(1) C$_{1-8}$ alkyl, wherein said C$_{1-8}$ alkyl is straight, branched or cyclic, may contain one or two double or triple bonds, and is unsubstituted or substituted with one or more of the substituents selected from:
(i) hydroxy,
(ii) oxo,
(iii) fluoro,
(iv) amino,
(v) Ar$_1$, wherein Ar$_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from:
hydrogen, halogen, hydroxy, C$_{1-6}$ alkyl, —O(C$_{1-6}$ alkyl), —NO$_2$, —CN, —SO$_2$NH$_2$, —SO$_2$NH(C$_{1-6}$ alkyl), —SO$_2$N(C$_{1-6}$ alkyl)(C$_{1-6}$ alkyl), amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —NHSO$_2$(C$_{1-6}$ alkyl), —N(C$_{1-6}$ alkyl)SO$_2$(C$_{1-6}$ alkyl), —SO$_2$NHCO(C$_{1-6}$ alkyl), —CONHSO$_2$(C$_{1-6}$ alkyl), —CON(C$_{1-6}$ alkyl)

($C_{1-6}$ alkyl), —$CO_2$($C_{1-6}$ alkyl), —S($C_{1-6}$ alkyl), —SO($C_{1-6}$ alkyl), or —$SO_2$($C_{1-6}$ alkyl), wherein $C_{1-6}$ alkyl, is defined as above, (vi) —$NR_5R_6$, wherein $R_5$ and $R_6$ are independently selected at each occurrence from:
(a) hydrogen,
(b) $C_{1-6}$ alkyl, wherein $C_{1-6}$ alkyl is as defined above,
(c) —$(CH_2)$n-$Ar_1$, wherein n is independently selected at each occurrence from 0, 1 or 2,
(d) or the groups $R_5$ and $R_6$ are joined together to form a 4- to 8-membered ring which may contain one or two double bonds, or one or two oxo, or one or two O, S or N—$R_7$ wherein $R_7$ is independently selected at each occurrence from hydrogen, $C_{1-6}$ alkyl, —$(CH_2)$n-$Ar_1$, (vii) —$OR_5$, wherein $R_5$ is as defined above,
(viii) —$CONR_5R_6$ wherein $R_5$ and $R_6$ are as defined above,
(ix) —$CO_2R_5$, wherein said $R_5$ is as defined above;

(2) $Ar_2$, wherein $Ar_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and is unsubstituted and substituted with one or more substituents selected from: hydrogen, halogen, hydroxy, $C_{1-8}$ alkyl, —O($C_{1-8}$ alkyl), —$NO_2$, —CN, —$SO_2NH_2$, —$SO_2NH$($C_{1-8}$ alkyl), —$SO_2N$($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO($C_{1-8}$ alkyl), or —$SO_2$($C_{1-8}$ alkyl), wherein said $C_{1-8}$ alkyl is as defined above;

(3) —$NR_8R_9$, wherein $R_8$ and $R_9$ are independently selected at each occurrence from:
(a) hydrogen,
(b) $Ar_2$,
(c) $C_{1-8}$ alkyl, wherein said $C_{1-8}$ alkyl is as defined above;
or the groups $R_8$ and $R_9$ are joined together to form a which ring may contain one or more double bonds; one or more oxo; one or more O, S(O)n, N—$R_7$ wherein n and $R_7$ are as defined above; or one or more of hydroxy, halogen, amino, $C_{1-8}$ alkyl, —O($C_{1-8}$ alkyl), —$NO_2$, —CN, —$SO_2NH_2$, —$SO_2NH$($C_{1-8}$ alkyl), —$SO_2N$($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO($C_{1-8}$ alkyl), or —$SO_2$($C_{1-8}$ alkyl); and (4) —$OR_8$;

$R_4$ is
hydrogen, halogen, hydroxy, $C_{1-8}$ alkyl, —O($C_{1-8}$ alkyl), —$NO_2$, —CN, —$SO_2NH_2$, —$SO_2NH$($C_{1-8}$ alkyl), —$SO_2N$($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$ ($C_{1-8}$ alkyl), —$NHSO_2$($C_{1-8}$ alkyl), —N($C_{1-6}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO ($C_{1-8}$ alkyl), —$SO_2$($C_{1-8}$ alkyl), or $Ar_2$;

$Y_1$ is —$CR_{11}R_{12}$—, —$CR_{11}R_{12}(CH_2)_p$—, or $(CH_2)_p CR_{11}R_{12}$ where
p is 0, 1, or 2;
$R_{11}$ and $R_{12}$ are independently selected at each occurrence from:
(1) hydrogen; and
(2) $C_{1-8}$ alkyl; and the M ring is a 5- to 8-membered ring which may contain one or more double bonds, one O, S(O)n or N—$R_7$, wherein n and $R_7$ are as defined above, and which ring may be substituted with one or more of hydroxy, halogen, amino, $C_{1-8}$ alkyl, —O($C_{1-8}$ alkyl), —$NO_2$, —CN, —$SO_2NH_2$, —$SO_2NH$($C_{1-8}$ alkyl), —$SO_2N$($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO ($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2NHCO$ $C_{1-8}$ alkyl), —$CONHSO_2$ ($C_{1-8}$ alkyl), —CON($C_{1-8}$ alkyl)($C_{1-8}$ alkyl), —$CO_2$($C_{1-8}$ alkyl), —S($C_{1-8}$ alkyl), and —SO ($C_{1-8}$ alkyl).

11. A compound according to claim 10, wherein $R_3$ is optionally substituted phenyl.

12. A compound according to claim 11, wherein $R_1$ is hydrogen or fluorine.

13. A compound according to claim 11, wherein the M ring is a 5–7 membered ring having one nitrogen, where each carbon in the M ring is optionally substituted with methyl or ethyl.

14. A compound of the formula

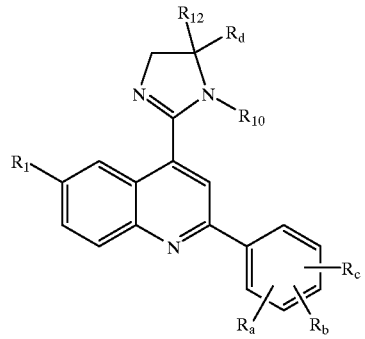

or a pharmaceutically acceptable salt or solvate thereof where $R_a$, $R_b$, and $R_c$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl) ($C_{1-6}$ alkyl), —$CO_2$($C_{1-6}$ alkyl);

$R_1$ is hydrogen or fluorine;

$R_{12}$ is hydrogen or $C_{1-8}$ alkyl; and $R_d$ and $R_{10}$ together form an alkylene group of from 3–5 carbon atoms each of which is optionally substituted with methyl or ethyl.

\* \* \* \* \*